United States Patent [19]

Poidomani

[11] 3,998,228

[45] Dec. 21, 1976

[54] EXTERNAL CATHETERIZE DEVICE FOR MALES

[76] Inventor: Vincent Poidomani, 2448 E. First St., Brooklyn, N.Y. 11223

[22] Filed: Oct. 14, 1975

[21] Appl. No.: 621,645

[52] U.S. Cl. .............................................. 128/295
[51] Int. Cl.² .......................................... A61F 5/44
[58] Field of Search .................. 128/294, 295, 2 F; 4/110

[56] References Cited

UNITED STATES PATENTS

| | | | |
|---|---|---|---|
| 1,229,423 | 6/1917 | Eckenrode | 128/295 |
| 1,379,289 | 5/1921 | Rogers | 128/295 |
| 2,310,505 | 2/1943 | Blackburn et al. | 128/295 |
| 3,339,551 | 9/1967 | Stoutenburgh | 128/295 |
| 3,353,538 | 11/1967 | Carrigan | 128/295 |
| 3,369,546 | 2/1968 | Hickok | 128/295 |
| 3,394,703 | 7/1968 | Orgel | 128/295 |
| 3,608,552 | 9/1971 | Broerman | 128/295 |
| 3,721,243 | 3/1973 | Hesterman et al. | 128/295 |
| 3,739,783 | 6/1973 | Broerman | 128/295 |
| 3,788,324 | 1/1974 | Lim | 128/295 |

*Primary Examiner*—Clifford D. Crowder
*Attorney, Agent, or Firm*—Richard L. Miller

[57] ABSTRACT

A device for use by males who are unable to retain urine between normal periodic urination so that they are subject to bed-wetting; the device consisting of a sheath into which the penis is inserted, the sheath being of basket woven design so that when stretched, it binds around the penis so to not fall off therefrom, the sheath being lined with a water proof liner, one end of the sheath being connected by a flexible hose to a urine collection container conveniently placed nearby.

1 Claim, 4 Drawing Figures

EXTERNAL CATHETERIZE DEVICE FOR MALES

This invention relates generally to appliances for being worn by patients having physical debilities.

A principal object of the present invention is to provide an appliance for being worn by a male patient who does not have the capacity to retain urine between normal periods of urination, the appliance preventing the objectionable situation of bed wetting by such persons.

Another object is to provide a device which may be made in various sizes so to be suitable for use by infants, boys of various ages or by grown men.

Other objects are to provide a device that is simple in design, inexpensive to manufacture, rugged in construction, easy to use, and will not fall off accidentally and is efficient in operation.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

Figure 1:
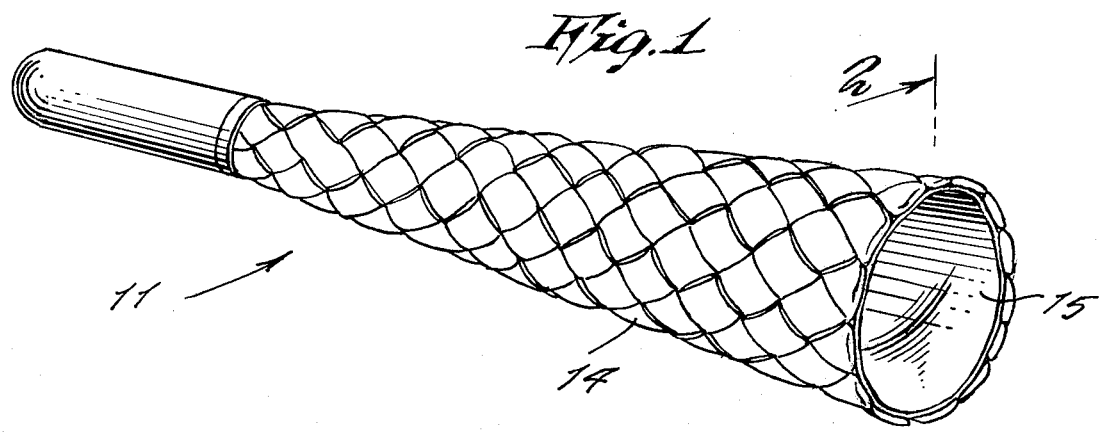
Figure 2:
Figure 2:
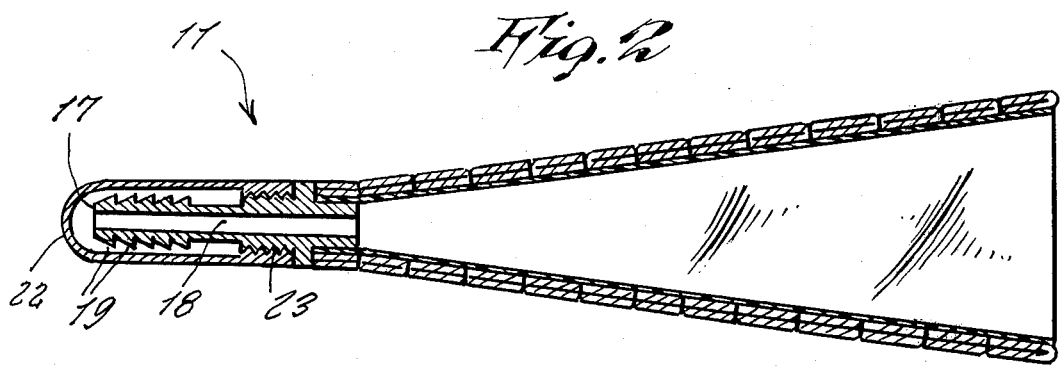
Figure 3:
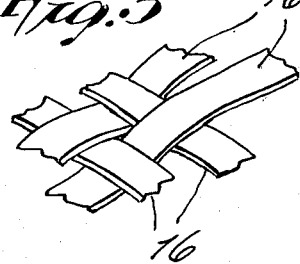
Figure 4:
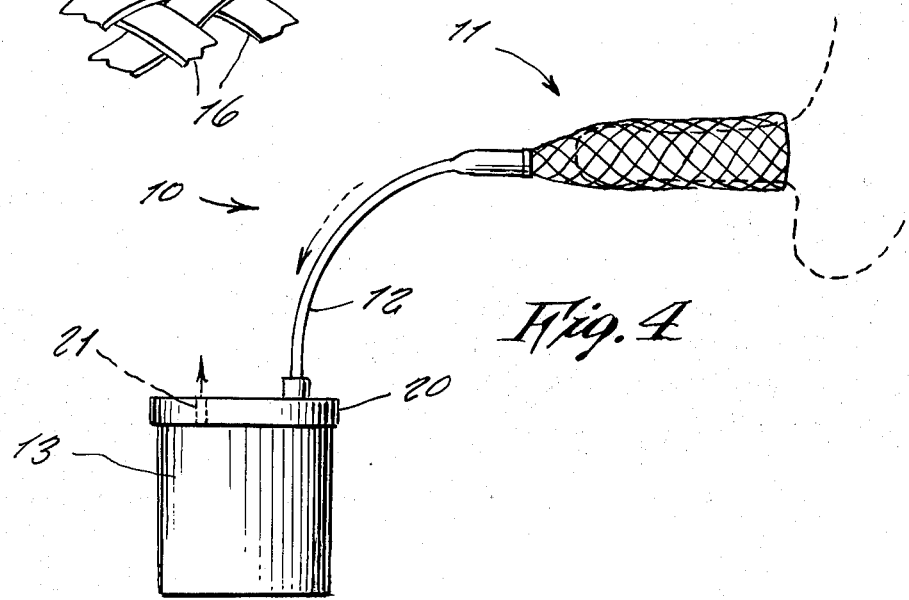

FIG. 1 is a perspective view of the invention.
FIG. 2 is a cross section on line 2—2 of FIG. 1.
FIG. 3 is a detail of the weave of the socket outer layer.
FIG. 4 is a side view showing the invention in use.

Referring now to the drawing in detail, the reference numeral 10 represents a device according to the present invention and which the inventor prefers to term as an External Catheterize Device for Males. Its construction includes a sheath 11 of generally conical shape connectable at its narrow end to a flexible hose 12 leading into a container 13.

The sheath is constructed of an outer case 14 having an inner liner 15. The case is made of flat strips 16 of synthetic or metallic fibers, and which are woven together in a basket weave pattern as clearly shown in FIG. 3. As clearly shown in FIGS. 1 and 4 of the drawing, the basket weave extends diagonally respective to a longitudinal axis of the sheath; the flat strips 16 that interweave each other, accordingly being left and right spiral shaped so that when the sheath is longitudinally stretched, then the sheath diameter is contracted so to bind on the penis.

In a size for an adult man, the sheath may be made 10 inches long, one end being one inch in diameter and the narrow end being one-half inch in diameter.

The liner 15 is made of flexible, thin, waterproof plastic film.

The narrow end of the liner and case are secured around a nipple 17 made preferably of a rigid plastic so that it is unaffected by urine acid and so that it is washable. A central opening 18 extends through the nipple, and an exposed protruding end of the nipple has annular teeth 19 so that an end of the hose 12 will firmly hold thereupon. The hose is made of plastic for the same reasons as indicated above.

The container 13, also of plastic, includes a removable cover 20 so that the container can be emptied and cleaned. An air vent 21 is provided through the cover.

In use, the sheath basket weave permits the sheath to be longitudinally contracted so that its diameter is sufficiently enlarged in order to allow insertion of the penis therewithin, after which the sheath is longitudinally stretched so that its diameter contracts thus binding around the penis so to not fall off.

Thus there is provided a device that is easy to put on or take off, and which is comfortable to a wearer while laying in bed; the container being at a lower lever such as on a floor.

When the sheath is detached from the hose, a closed end cap 22 of rigid plastic is screw threaded on thread 23 of the nipple so to enclose the same.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. An external catheterize device for males, comprising in combination, a sheath, a flexible hose attachable at one end to one end of said sheath, and a container connected to an opposite end of said hose; said sheath having self contained means for frictionally holding on a penis that is inserted thereinto; said sheath being of generally conical shape, a narrower end of said sheath being attached to said hose while a larger end receives said penis, said sheath consisting of an outer case made of a plurality of crossing interwoven, flexible, right and left spiral shaped, flat strips forming a basket weave that runs diagonally respective to a longitudinal axis of said sheath, said sheath accordingly being enlarged in diameter when longitudinally contracted so to receive said penis, and being diametrically contracted when longitudinally stretched so to bind on said penis, a flexible, thin, waterproof plastic liner of conical shape on an inner side of said case, said sheath having a length that is ten times the diameter of said larger end, and said narrower end having a diameter that is one-half said larger end; a rigid nipple being secured at said narrower end of said sheath, said nipple having a central opening therethrough, an external thread around one end of said nipple engaging a threaded end-cap when said hose is not connected to said nipple, an opposite end of said nipple having a row of annular teeth for firmly grasping said hose end, and said container including a removable lid to which said hose opposite end is affixed, said container cover having an air vent.

* * * * *